(12) United States Patent
Walder et al.

(10) Patent No.: US 10,376,887 B2
(45) Date of Patent: Aug. 13, 2019

(54) CLOSING ARRANGEMENT AND METHOD OF CLOSING TUBE

(71) Applicants: QIAGEN GMBH, Hilden (DE); QIAGEN INSTRUMENTS AG, Hombrechtikon (CH)

(72) Inventors: Bruno Walder, Hombrechtikon (CH); Sasa Lazevski, Hilden (DE); Kurt Stark, Berg (CH)

(73) Assignee: Qiagen GMBH, Hilden (DE)

( * ) Notice: Subject to any disclaimer, the term of this patent is extended or adjusted under 35 U.S.C. 154(b) by 537 days.

(21) Appl. No.: 14/782,010

(22) PCT Filed: Apr. 9, 2014

(86) PCT No.: PCT/EP2014/057122
§ 371 (c)(1),
(2) Date: Oct. 2, 2015

(87) PCT Pub. No.: WO2014/166980
PCT Pub. Date: Oct. 16, 2014

(65) Prior Publication Data
US 2016/0030938 A1    Feb. 4, 2016

(30) Foreign Application Priority Data
Apr. 9, 2013  (EP) .................................... 13162967

(51) Int. Cl.
*B01L 3/00*      (2006.01)
*B65B 7/28*      (2006.01)
(Continued)

(52) U.S. Cl.
CPC ............ *B01L 3/50825* (2013.01); *B01L 9/06* (2013.01); *B65B 7/28* (2013.01); *G01N 35/04* (2013.01);
(Continued)

(58) Field of Classification Search
CPC ............ G01N 2035/0405; G01N 35/04; B01L 2300/043; B01L 3/50825; B01L 2200/025; B01L 9/06; B65B 7/28
(Continued)

(56) References Cited

U.S. PATENT DOCUMENTS

| | | | |
|---|---|---|---|
| 5,628,962 A | * | 5/1997 | Kanbara ................. B01L 99/00 215/235 |
| 2001/0013169 A1 | | 8/2001 | Fassbind et al. |

(Continued)

FOREIGN PATENT DOCUMENTS

| | | |
|---|---|---|
| DE | 4439755 A1 | 5/1996 |
| DE | 102010029136 A1 | 11/2011 |

(Continued)

OTHER PUBLICATIONS

International Search Report from corresponding PCT/EP2014/057122, dated May 28, 2014.

*Primary Examiner* — Robert F Long
*Assistant Examiner* — Xavier A Madison
(74) *Attorney, Agent, or Firm* — McBee Moore Woodward & Vanik IP, LLC

(57) ABSTRACT

Closing arrangement for a cap of a tube in a carrier, wherein the arrangement comprises at least a first, a second and a third moveable engagement member, the first member being adapted to induce a first part of the cap rotation and the second member being adapted to induce a second part of the cap rotation and the third member being adapted to induce a third part of the cap rotation for closure.

11 Claims, 3 Drawing Sheets

(51) Int. Cl.
*B01L 9/06* (2006.01)
*G01N 35/04* (2006.01)
(52) U.S. Cl.
CPC ... *B01L 2200/025* (2013.01); *B01L 2300/041* (2013.01); *B01L 2300/042* (2013.01); *B01L 2300/043* (2013.01); *G01N 2035/0405* (2013.01)
(58) Field of Classification Search
USPC .................................. 53/381.1, 489
See application file for complete search history.

(56) References Cited

U.S. PATENT DOCUMENTS

| | | | |
|---|---|---|---|
| 2001/0028863 A1* | 10/2001 | Kitagawa | B65D 21/0204 422/509 |
| 2007/0110624 A1* | 5/2007 | Lare | G01N 35/00 422/400 |

FOREIGN PATENT DOCUMENTS

| | | |
|---|---|---|
| EP | 0979999 A2 | 2/2000 |
| JP | S6461667 A | 3/1989 |
| JP | 64061667 | 8/1989 |
| JP | 11166933 A | 6/1999 |
| JP | 11511846 A | 10/1999 |
| JP | 200172185 A | 3/2001 |
| JP | 2007511420 A | 5/2007 |
| JP | 2009109403 A | 5/2009 |
| WO | 2011144658 A1 | 11/2011 |
| WO | 2012006668 A1 | 1/2012 |

\* cited by examiner

CLOSING ARRANGEMENT AND METHOD OF CLOSING TUBE

CROSS REFERENCE TO RELATED APPLICATIONS

This application is a § 371 National Stage Application of PCT/EP2014/057122, filed 9 Apr. 2014, which claims priority to EP 13162967.7, filed 9 Apr. 2013.

BACKGROUND

Field of the Invention

The invention pertains to a closing arrangement for a cap of a tube on a carrier. Especially, the invention relates to a tube which can contain fluid for in vitro amplification reaction, PCR and/or genotyping.

Description of Related Art

In vitro amplification procedures can be carried out in a small reaction tube which can be positioned within a thermal cycler or another laboratory device. The thermal cycler heats and cools the PCR tubes to achieve the specific temperatures required, especially the specific temperatures required for the polymerase chain reaction. The thermal cycler can provide a rotor or block for handling reaction vessels such as the tubes, especially for rotating the tubes (rotor) and/or heating and cooling.

In operation, a tube is filled with a (biological) fluid and sealed with a cap which can be connected to or integrally formed with the tube.

WO 2012/006668 A1 discloses a multi vessel ring which comprises a ring body and a plurality of elongate tubes, each elongate tube being integrally formed with the ring body. The multi vessel ring further comprises a plurality of caps, each cap being integrally formed with the ring body, and adapted to seal one of the tubes. WO 2012/006668 A1 discloses a capping tool which has a primary unit and a secondary unit. For capping the tubes, the tubes have to be pivoted.

SUMMARY

It has been found that the capping which involves pivoting of the tubes causes difficulties because the pivoted tubes require increased handling skills.

It is an object of the invention to provide for a closing arrangement and a method for closing which overcomes the difficulties of handling pivoted tubes.

The object is solved by the subject-matter of the independent claims.

It has been found that a closing arrangement for a cap of a tube in a carrier can be used which comprises three moveable engagement members to close the tubes. Preferably, the tubes do not have to be pivoted. Preferably, the cap movement for closure is a rotation with regard to the tube.

DETAILED DESCRIPTION OF A PREFERRED EMBODIMENT

Figure 1:
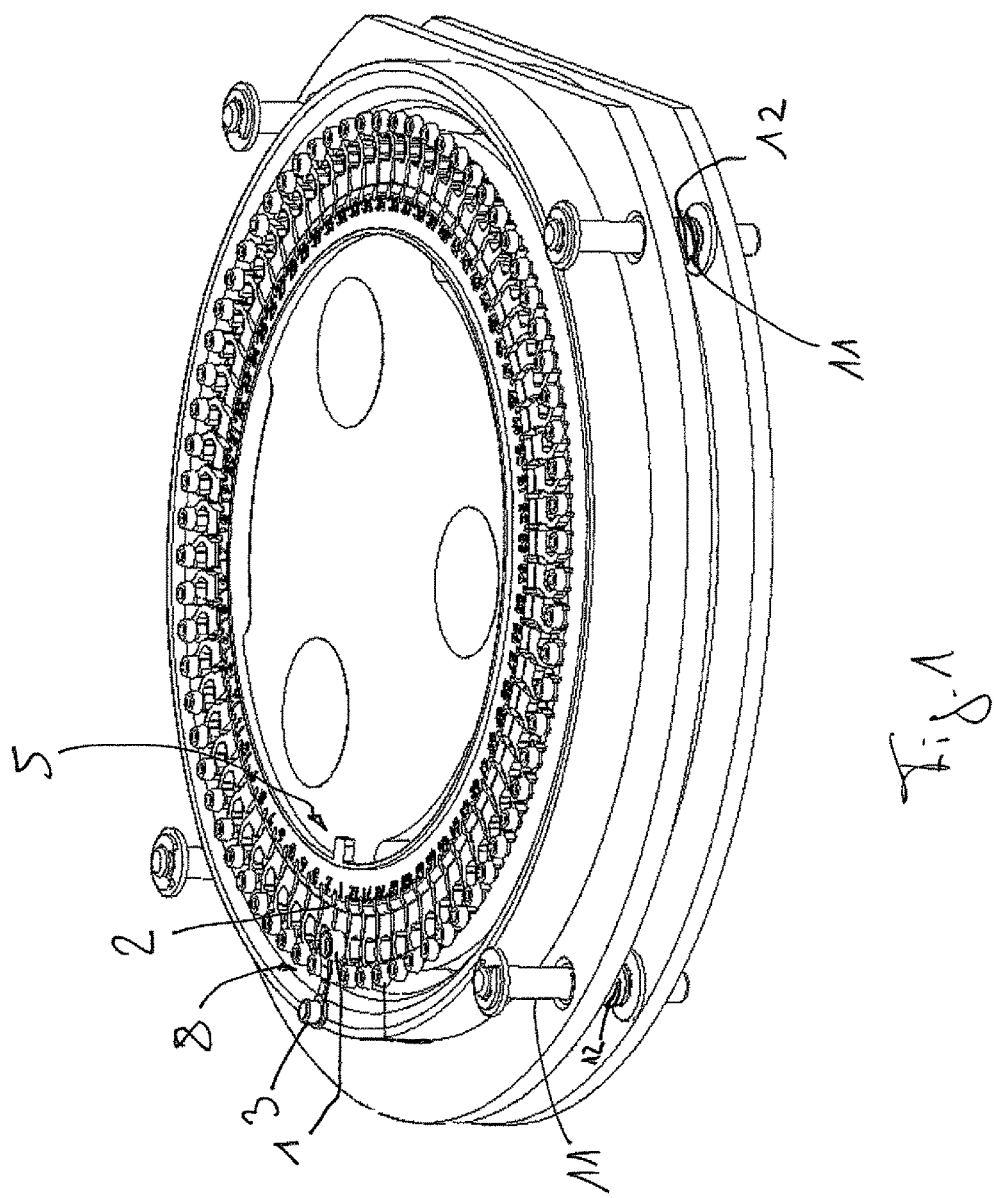
FIGS. 1-16 depict embodiments of the disclosure described herein.

Preferably, the three moveable engagement members move in an uni-axial direction.

In a preferred embodiment, the three moveable engagement members are guided coaxially to one another in consecutive steps. Several blocks and springs can be provided according to which the total movement can be separated into partial motion in each consecutive step. This allows for a simple assembly.

The tube can be a disposable tube and can be produced by injection moulding from a plastic material suitable for in vitro amplification processes. Preferably, the tube has a volume in the interval 0.05 to 2.0 ml, especially preferably 0.2 to 0.6 ml.

The term "biological fluid" which can be filled in the tube encompasses especially blood, DNA, RNA, nucleic acids, oligonucleotides and/or aptamers.

The term "carrier" encompasses every structure which allows for positioning of more than 3 tubes in such that the tubes and the carrier can be handled as a unit, especially the carrier can be formed as an adapter. Thus, grabbing the carrier leads to the possibility to handle and/or move or carry the tubes positioned in the carrier. The carrier can be positioned for example in a rotor or similar device of a thermal cycler.

In a preferred embodiment, the three engagement members comprise an inclined surface, a guide finger, and a pushing element, wherein the inclined surface is adapted for engagement with the cap and for a transfer of movement of the cap relative to the tube, wherein the inclined surface is further adapted as a guidance for the guide finger.

Preferably, the inclined surface and the guide finger are adapted for a relative translatory movement towards each other, and the guidance of the inclined surface allows for a sliding movement of the guide finger relative to the block. This allows for a simple mutual guidance enabling coordinated movement for closing the cap. The guide finger elastically deforms when the guide finger slides on the inclined surface. The guide finger has elastic and/or resilient property with regard to flexure and/or bending in the lateral direction. However, the guide finger is stiff in the longitudinal direction. The afore-mentioned guide finger can be formed or embellished as a closing or recoil spring.

The inclined surface can be formed by a block or a toroidal part, comprising a chamfer or bevel.

Preferably, the inclined surface is supported by pins which can be subjected to spring tension.

In a preferred embodiment, the guide finger comprises a section with a slope which can substantially resemble the incline of the inclined surface. The slope and the incline can substantially correspond to each other. In case that slope and incline substantially resemble each other, the initially movement of the guide finger contacting the inclined surface is assisted.

Preferably, the inclined surface and the guide finger are positioned outside the circumferential area of the carrier.

Further, the carrier can comprise receptacles for the tubes which are circumferentially partially open. However, it is not a requirement. Essential is that the tube is held in the receptacle. The receptacle can also be circumferentially closed. The receptacles can have an elastic connection to the carrier to enable a pivoting of the tubes.

Other objects, features, advantages and aspects of the present application will become parent to those skilled in the art from the following description and dependent claims. It should be understood, however, that the following description, dependent claims and specific examples, while indicating preferred embodiments of the application, are given by a way of illustration only. Various changes and modifications within the spirit and scope of the disclosed invention will become really apparent to those skilled in the art reading the following.

Figure 2:
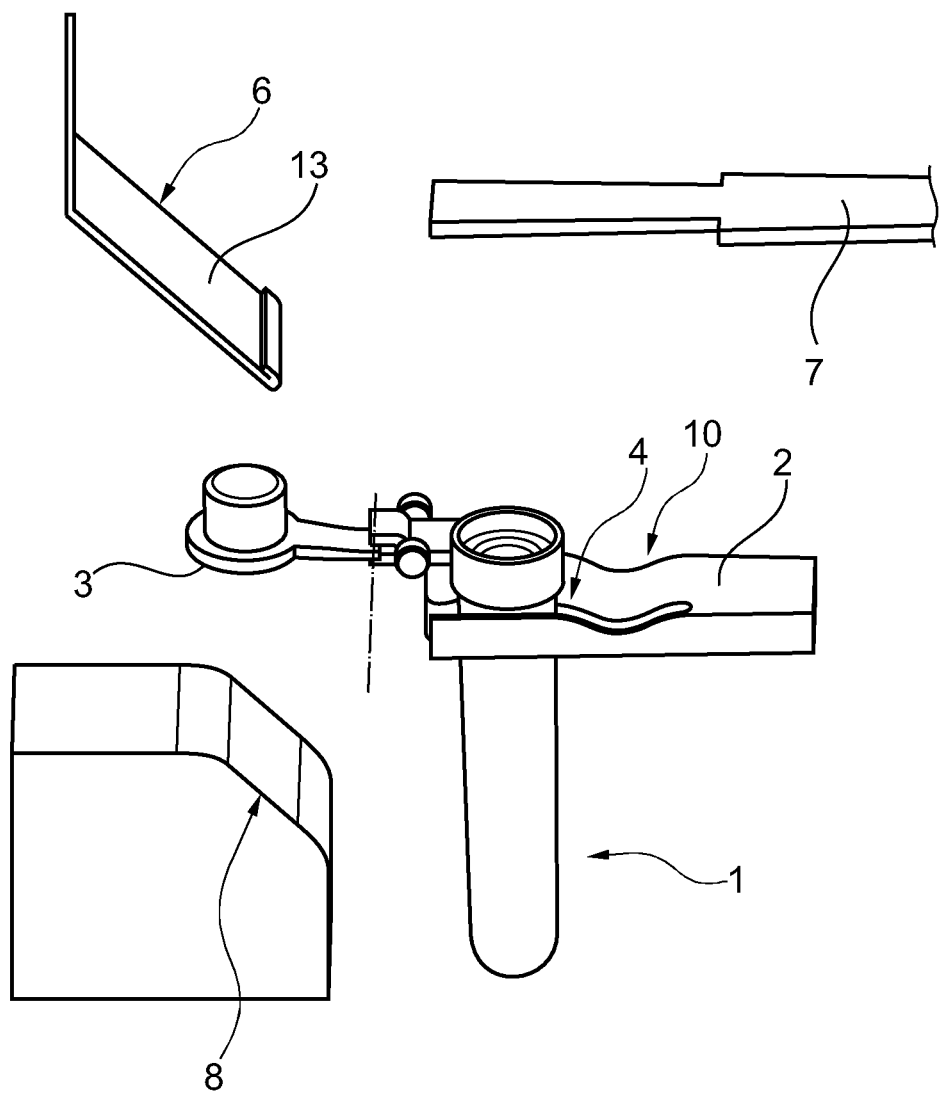

Examples of the invention will now be described with references to the accompanying drawings in which:

FIG. 1 schematically shows a tube in a carrier together with a closing arrangement according to the invention;

FIG. 2 schematically shows a perspective view of the tube in a carrier with an inclined surface;

FIGS. 3 to 13 schematically show the stepwise closing of the tube; and

Figure 14:
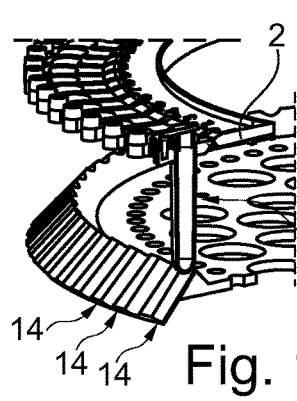
Figure 15:
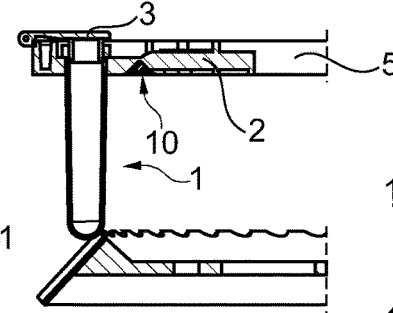
Figure 16:
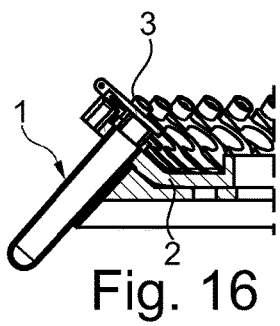

FIGS. 14 to 16 schematically show pivoting of the closed tube in the carrier.

FIG. 1 shows a tube 1 in a carrier 2, the tube 1 being in a straight alignment. The tube 1 is connected to a cap 3 for closing or sealing the tube 1. The tube 1 is arranged in a receptacle 4 of the carrier 2. The receptacle 4 is formed as a through-hole which has an opening at its circumference in the direction of the outer circumference of the carrier 2. The carrier 2 has a hinge 10 which is arranged as a film hinge in the carrier 2 made of plastic material or a polymer.

A closing arrangement for the cap 3 of the tube 1 in the carrier 2 is shown in FIG. 1. The closing arrangement comprises at least three moveable engagement members, which can be each subjected to an uni-axial movement. The three moveable engagement members can be guided coaxially to one another.

The three engagement members comprise a fixture or holder 5 for the carrier 2, a guide finger 6, and a pushing element 7, wherein an inclined surface 8 is adapted for engagement with the cap 3 and for a transfer of movement of the cap 3 relative to the tube 1, wherein the inclined surface 8 is further adapted as a guidance for the guide finger 6.

Figure 3:
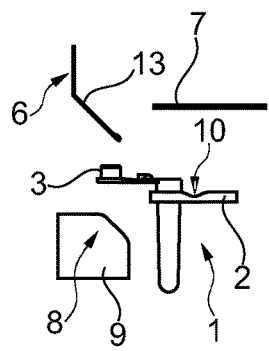
Figure 4:
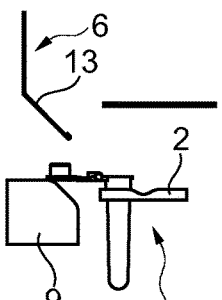
Figure 5:
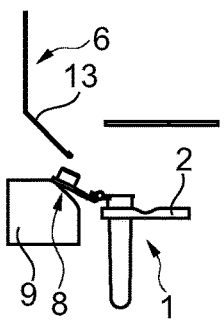
Figure 6:
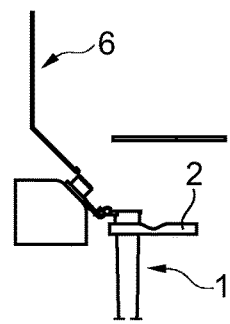
Figure 7:
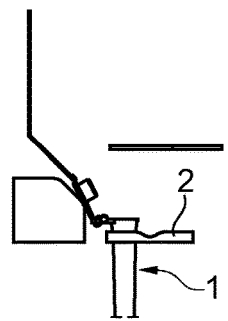

FIGS. 3 to 8 show that the inclined surface 8 which is provided by a ring 9, comprising a bevel or a chamfer comprising the inclined surface 8, moves relative to the cap 3 of the tube 1. In FIG. 3 it is shown that the ring 9 touches the cap 3 and upon further movement of the ring 9, the cap 3 comes into abutment with the inclined surface 8. The relative movement of the tube 1 with the cap 3 with regard to the inclined surface 8 is provided by movement of the holder 5 relative to the ring 9 which remains inactive (not driven or moved). FIG. 2 shows the support of the ring 9. Ring 9 is supported by pins 11 which can be subjected to spring tension by a spring 12.

The abutment with the ring 9 and the inclined surface 8 causes an initial movement of the cap 3 with regard to the tube 1 into the closing position of the cap 3. In FIGS. 3 to 8 it is shown that the carrier 2 is moved together (downwardly) with the guide finger 6 and the pushing element 7 in an uni-axial direction. In the progress of closing the cap 3 the three elements move into stop positions which are predetermined by dogs and/or blocks preventing a further movement of the respective element.

Figure 8:
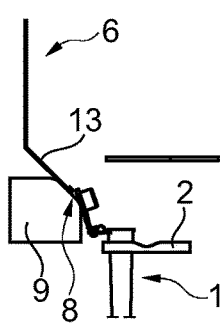

In FIG. 8 it is shown that the movement of the holder 5 together with the carrier 2 comes to a stop. Further, it is shown that the guide finger 6 touches the inclined surface 8.

Figure 9:
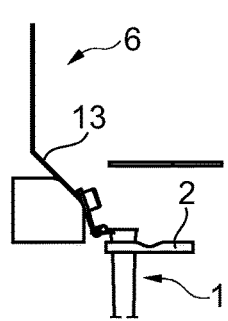
Figure 10:
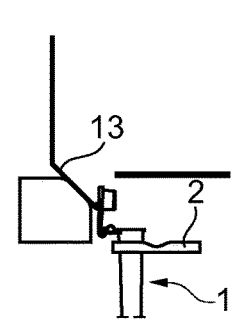
Figure 11:
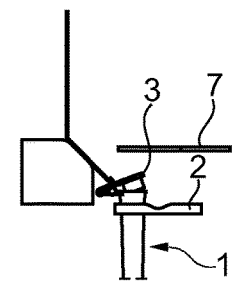
Figure 12:
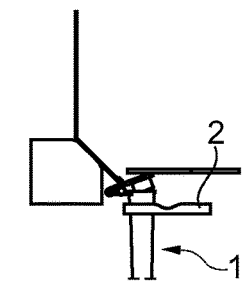

Upon further movement of the guide finger 6 relative to the holder 5, the guide finger 6 moves translatory with regard to ring 9 and the inclined surface 8. The guide finger 6 can bend elastically when contacting the ring 9 and the inclined surface 8. The guide finger 6 slides on the ring 9 on the inclined surface 8. Upon further movement of the guide finger 6, the guide finger 6 pushes the cap 2 further into its closing position (FIGS. 9 to 11). The guide fingers 6 glide on the inclined surface 8 towards the center defined by the center of the ring 9 or the carrier 2. The guide finger 6 can comprise a section 13 having a slope which can substantially resemble the incline of the inclined surface 8. The slope of section 13 may be different to the incline of the inclined surface 8. However, it is preferred that the slope and the incline have the same tendency or direction. The section 13 can assist when moving the guide finger 6 into the direction of the cap 2. Actually, the guide finger 6 deforms elastically when in contact with the inclined surface 8 so that the slope of section 13 changes as the shape of the guide finger 6 follows the shape of the inclined surface 8.

Figure 13:
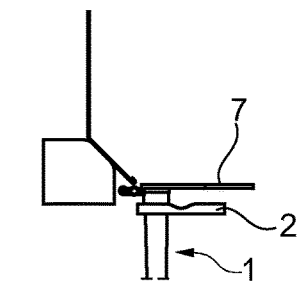

In FIG. 11 it is shown that the guide finger 6 comes to a stop. The pushing element 7 moves further in the direction of the cap 3. In the further movement of the pushing element 7 the cap 3 is closed and the pushing element 7 arrives at its stop position (FIG. 13).

In FIGS. 14 to 16 it is shown that the outer parts of the carrier 2 held by the holder 5 are pivoted with regard to the hinge 10. A sliding surface 14 for each of the tubes 1 is provided which is formed as a rounded cavity extending in its longitudinal direction with a shape that corresponds to the outer surface of the tube 1.

The invention claimed is:

1. Closing arrangement for a cap of a tube in a carrier, wherein the arrangement comprises at least three moveable engagement members, wherein the three moveable engagement members are guided coaxially to one another to close the cap of the tube,
   wherein the three engagement members comprise a fixture for the carrier, a guide finger, and a pushing element, wherein an inclined surface is adapted for engagement with the cap and for a transfer of movement of the cap relative to the tube, wherein the inclined surface is further adapted as a guidance for the guide finger; and
   wherein the inclined surface and the guide finger are adapted for a relative translatory movement towards each other, and the guidance of the inclined surface allows for a sliding movement of the guide finger relative to the inclined surface.

2. Closing arrangement according to claim 1, wherein the three moveable engagement members are each capable of being subjected to a uni-axial movement.

3. Closing arrangement according to claim 1, wherein the inclined surface is provided by a ring comprising a chamfer and/or bevel.

4. Closing arrangement according to claim 1, wherein the inclined surface is supported by pins subjected to spring tension.

5. Closing arrangement according to claim 1, wherein the guide finger comprises a section with a slope which resembles an incline of the inclined surface.

6. Closing arrangement according to claim 1, wherein the inclined surface and the guide finger are positioned outside a circumferential area of the carrier.

7. Closing arrangement according to claim 1, wherein the carrier comprises one or more receptacles for one or more tubes which are circumferentially partially open.

8. Method of closing tubes, each tube being connected with a cap, the tubes being arranged on a carrier, wherein an inclined surface, a guide finger, and a pushing element are provided, wherein the method comprises: moving a cap by the inclined surface, impinging the guide finger on the inclined surface, guiding the guide finger by the inclined surface, moving the cap by impact of the guide finger, pushing the cap by the pushing element to close the cap.

9. Method according to claim 8, wherein the tubes are held in an upright position without pivoting.

10. Method according to claim 8, wherein the guide finger is moved uni-axially towards the inclined surface and the guide finger glides laterally on the inclined surface towards a center.

11. Method according to claim 8, wherein the movement caused by the inclined surface is an initial movement of the cap, and the movement caused by the guide finger is a movement of the cap until abutment of the cap on an open end of the tube.

* * * * *